US00PP20227P3

(12) United States Plant Patent
Jeske et al.

(10) Patent No.: US PP20,227 P3
(45) Date of Patent: Aug. 18, 2009

(54) HOP PLANT NAMED 'SUPER GALENA'

(50) Latin Name: *Humulus lupulus*
Varietal Denomination: Super Galena

(75) Inventors: Roger D. Jeske, Yakima, WA (US); Joe Brulotte, Yakima, WA (US)

(73) Assignee: S.S. Steiner, Inc., New York, NY (US)

( * ) Notice: Subject to any disclaimer, the term of this patent is extended or adjusted under 35 U.S.C. 154(b) by 199 days.

(21) Appl. No.: 11/344,257

(22) Filed: Jan. 31, 2006

(65) Prior Publication Data

US 2007/0033684 P1 Feb. 8, 2007

(51) Int. Cl.
*A01H 5/00* (2006.01)

(52) U.S. Cl. ..... Plt./236

(58) Field of Classification Search ..... Plt./236
See application file for complete search history.

*Primary Examiner*—Susan B McCormick Ewoldt
(74) *Attorney, Agent, or Firm*—Hayes Soloway P.C.

(57) ABSTRACT

A novel variety of hop, *Humulus lupulus* L., named "Super Galena" is disclosed. "Super Galena" has relatively high contents of bitter acids, beta-acids, total oil, and humulene, and a moderate, pleasant aroma. "Super Galena" is comparable to Galena in its aroma and bitterness profile but offers a substantially higher yield and complete resistance to hop powdery mildew strains found in Washington, United States. The new variety was discovered among the progeny of a sexual cross made in 1998 in Yakima, Wash., United States and has been asexually reproduced and assessed in field plots in Prosser, Wash., United States.

2 Drawing Sheets

BACKGROUND OF INVENTION

The flowers (cones) of the female hop plant, *Humulus lupulus* L, are used in the making of beverages, especially beer, as a flavoring and processing component. Hops contribute towards the bitterness and aroma in beer as well as foam quality and flavor and taste stability.

Hop plants, hops cones, male hop flowers, hop plant parts, hop tissue cultures and hop extracts also have bioactive properties; including anti-microbial, anti-cancer, anti-osteoporosis, anti-oxidative, anti-inflammatory, antibiotic, soporific, anti-androgenic, and pro-estrogenic activities, among others; which may be used in herbal remedies, in antimicrobial preparations for food, fodder, food fermentation, food process, animal husbandry; or in non-food uses, such as composting, biofuel processing, fermentation process, water treatment, animal bedding and phytoremediation; and uses in cosmetics, in nutraceutical and in pharmaceutical applications and in research thereof. Examples activities and non-beverage uses are included herein by references: J Hazard Mater. Apr 26;91(1–3):95–112; Mol Cancer Ther. Sep;1(11):959–69; Phytochemistry. May;65(10):1317–30; U.S. Pat. No. 6,423,317 (2002); U.S. Pat. No. 6,623,775 (2003).

Agricultural end-product users, growers, handlers and processors of hops, of hop plants, of hop tissues and of hop products use hops and are affected by the agronomic, developmental, morphological, chemical and physical properties that vary among unique and distinct asexually reproduced varieties. This invention relates to an asexually-produced hop variety, named "Super Galena", invented in a planned and systematically executed breeding program.

SUMMARY OF INVENTION

The novel hop variety "Super Galena", the invention described herein, is a female progeny of a controlled, sexual cross-pollination of a single male hop plant USDA 19058m (non-patented) and a single female hop plant "98001" (non-patented) performed in 1998 by Roger Jeske, one of the named inventors in a garden in Yakima, Wash. The parents of "98001" are female hop plant "Galena" (non-patented) and a male progeny (non-patented) of open pollinated "Nugget" (non-patented). Please note that the hop industry does not make or rely upon any comparisons between new varieties and their male parents or male grandparents because male hops have no commercial value. The comparison to the female parent is not known. During 1999 seeds collected from the above cross-pollination were germinated in a greenhouse in Prosser, Wash. These seedlings were planted in a field nursery and screened for gender, vigor, cone type, and disease resistance with the best genotypes being advanced to a single hill hop nursery during the spring of 2000. Mr. Jeske discovered the "Super Galena" variety during the summer of 2000 among the numerous hop genotypes growing in a single hill hop nursery in Prosser, Wash. These hop genotypes growing in the single hill hop nursery were grown in a 7'×7' spacing on twine attached to an 18' trellis system as are most commercially grown hops.

Chemical analysis and field observations of the hop plant "Super Galena" in 2000, demonstrated unusually high percentage of beta-acids compared to alpha-acids, lack of powdery mildew in the leaves and cones, and an exceptional cone set. Cones were compact, conical, and easy to pick with no shatter. Vigor was excellent and yield potential appeared to be exceptional, although yield data was not taken in 2000.

In 2001, "Super Galena" was asexually propagated in greenhouses at Prosser, Wash. Rhizomes from the original single hill plant of "Super Galena" were dug, divided and planted into multiple greenhouse grown containers. Softwood cuttings were periodically taken from these original containers until approximately 4,000 softwood-cutting plants were made. These plants constituted the first asexual reproduction of the "Super Galena" variety and represent the second generation. They were planted and grown in two different field locations with no powdery mildew observed and excellent production of beta-acids and alpha-acids at both locations during 2001. These two larger scale trials consisted of a multi-hill planting (7 plants) and a two-acre planting (1778 plants). Both were located in fields in Prosser, Wash. These trials were subjected to standard agronomic, cultural and management practices for the purpose of determining harvest ability, yield, chemical characteristic, and process ability.

During 2002, 2003, 2004, and 2005 asexually-reproduced, second-generation plants in the two field locations in Prosser, Wash. were sampled for chemical analysis and harvested for yield evaluations. Results from the test plots provided additional information supporting the disease resistance, yield potential, beta-acids and alpha-acids projections made from the original "Super Galena" plant (first generation) selected in 2000. This confirmed the unusually high beta-acids and alpha-acids percentages (total combined alpha and beta>23%), the low alpha to beta ratio of 1.6, and the exceptional yield of the new variety. The 2002–2005 commercially harvested two-acre test plots of second-generation plants grown at Prosser, Wash. produced 2600–3000 lbs./acre annually averaging 2750 lbs./acre over the four years. The commercially harvested hop cones were kiln dried to approximately 10% moisture, than were pressed into 200 lb. bales. Bale samples from the 2002–2005 second generation "Super Galena" hops grown in Prosser, Wash. field locations showed an average alpha-acids percentage of 14.5 and beta-acids percentage of 8.8% (ASBC spectrophotometric method), both slightly higher than the commercial public variety Galena (grandmother of "Super Galena"). Storage stability of second-generation hop cones compared favorably to the original "Super Galena" plant (first generation) selected in 2000. The average loss of alpha-acids of the harvested hop cones stored at room temperature (22° C.) for six months was 22%, which is very comparable to that of "Galena". Process ability into pellets and extract was satisfactory and comparable to "Galena".

In some hop varieties the seasonal time of vine elongation, which is determined by agronomic cultural practice, affects yield. In 2003, second generation plants in replicated plots within the two-acre trial in field locations in Prosser, Wash., were manually attached onto the trellis (training) on three different dates to effect early, mid and late training. All replications were harvested in Prosser, Wash. research facility. Vigor, growth habit, and yield were very similar for all treatments and chemical analysis of the hop cones showed alpha-acids and beta-acids production was nearly the same for all treatments. This is in contrast to "Galena" that when trained early will tend to flower early resulting in reduced overall growth and significantly lower yield.

In 2003, the second asexual reproduction of the "Super Galena" variety took place. The second-generation rootstock from the two acres was dug, divided and planted into a larger acreage test plot near Prosser, Wash. These third generation plants were grown in field locations in Prosser, Wash., utilizing standard agricultural practices that are common for hop production, except no powdery mildew fungicides application were made.

During 2003, 2004, and 2005 third generation plants grown in large trials in field locations in Prosser, Wash., were sampled for chemical analysis and harvested for yield evaluations. Results from this third generation large-scale test plot provided additional information supporting the powdery mildew resistance, exceptional yield, and high beta-acids and alpha-acids percentages.

Based on agronomic and chemical evaluations over a number of growing seasons both secondary and tertiary clones (second and third asexually-reproduced generations) of "Super Galena" exhibited genetic stability with respect to its novel characteristics of complete powdery mildew resistance, high yield (>2500 lb./ac), and high combined beta-acids and alpha-acids percentages (>23%) in multiple field locations in Prosser, Wash. This is in contrast to the mother "98001" and grandmother "Galena", both of which are susceptible to powdery mildew, have an average yield (1800–2200 lbs./ac), and have combined beta-acids and alpha-acids percentages of approximately 21%.

All observations, evaluations and testing of the "Super Galena" variety's agronomic, physical, morphological, and chemical properties were carried out by or directed by the inventors.

The variety "Super Galena" is usually ready to pick by the 15th to the 25th of September. The compact and ovoid shape cones of this variety are mid sized and plentiful resulting in easy mechanical picking and cleaning. Leaves do not develop in the cones, the cones detach easily from stems, and the cones do not shatter during commercial harvesting and drying.

In order to demonstrate genetic and phenotypic distinctiveness to closely related varieties, "Super Galena" is compared herein above to its mother and to agronomically important varieties below. "Galena" is in the pedigree of "Super Galena" and therefore similarities would be expected. The primary differences between the new "Super Galena" variety and "Galena" is the complete resistance of "Super Galena" to the powdery mildew strains found in the Yakima Valley and a >30% yield advantage of "Super Galena" verses "Galena". Similarities include a high percentage of beta acids as compared to alpha acids; similar cone shape and weight of 190–230 mg. at maturity, mature main vine of green coloration with no distinct stripe, and both varieties typically have five lobed dark green main vine leaves that are moderately serrated. Chemical similarities show that both have an alpha/beta ratio of 1.6, a humulene/caryophyllene ratio of 2.2, a CoH of 36–37%, and storage stability of 20–22% transformation of alpha acids after 6 months at 22° C.

The detailed botanical description and drawings herein below allow distinction of the variety from related varieties. For illustration, comparisons of select distinguishing traits to further selected commercial varieties are set forth in Table 1.

TABLE 1

| | "Super Galena" | "Galena" | "Nugget" | "Zeus" |
|---|---|---|---|---|
| Alpha acids % w/w | 13-16 | 10-13.5 | 11-14 | 12-16.5 |
| Beta acids % w/w | 8.0-10.0 | 7.0-9.0 | 4.0-6.0 | 4.0-6.0 |
| CoH % w/w of alpha acids | 35-40 | 35-40 | 24-30 | 27-35 |
| Total Oil ml/100 g | 1.5-2.5 | 0.9-1.2 | 1.5-3.0 | 1.0-2.0 |
| Humulene % | 19-24 | 10-15 | 12-22 | 10-25 |
| Caryophyllene % | 6-14 | 3.0-5.0 | 7-10 | 5.0-15 |
| Powdery Mildew Disease | Resistant | Susceptible | Resistant | Susceptible |

TABLE 1-continued

| | "Super Galena" | "Galena" | "Nugget" | "Zeus" |
|---|---|---|---|---|
| Cone Yield lbs/acre | 2500-2800 | 1600-2220 | 1700-2200 | 2400-3000 |

BRIEF DESCRIPTION OF THE DRAWINGS

The accompanying photographs illustrate the cones, leaves and growth habit of the new "Super Galena" variety.

GENERAL BOTANICAL DESCRIPTION OF THE VARIETY

Figure 1:
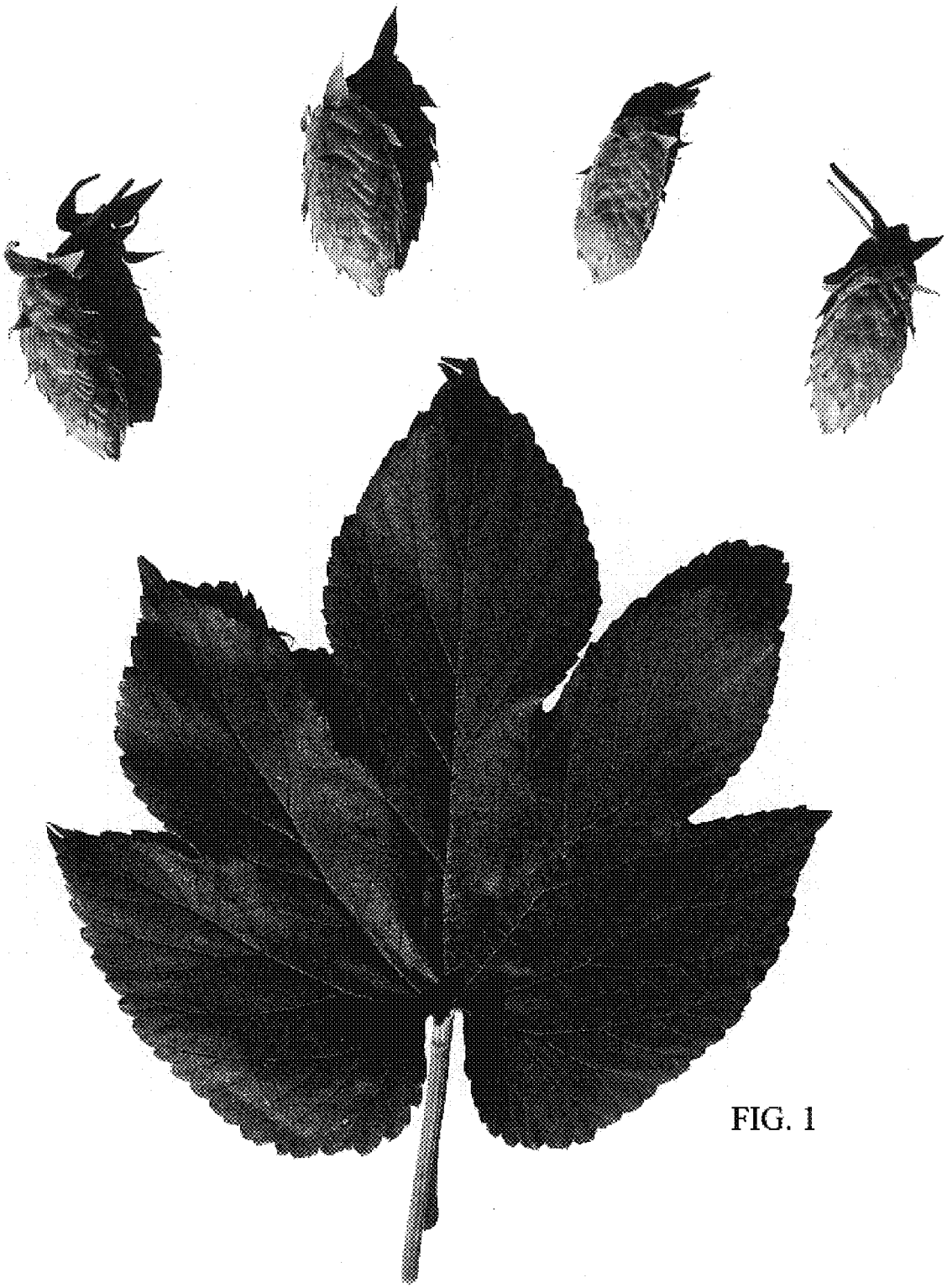
FIG. 1 depicts a close up of whole cones and a mature main vine leaf.
Figure 2:
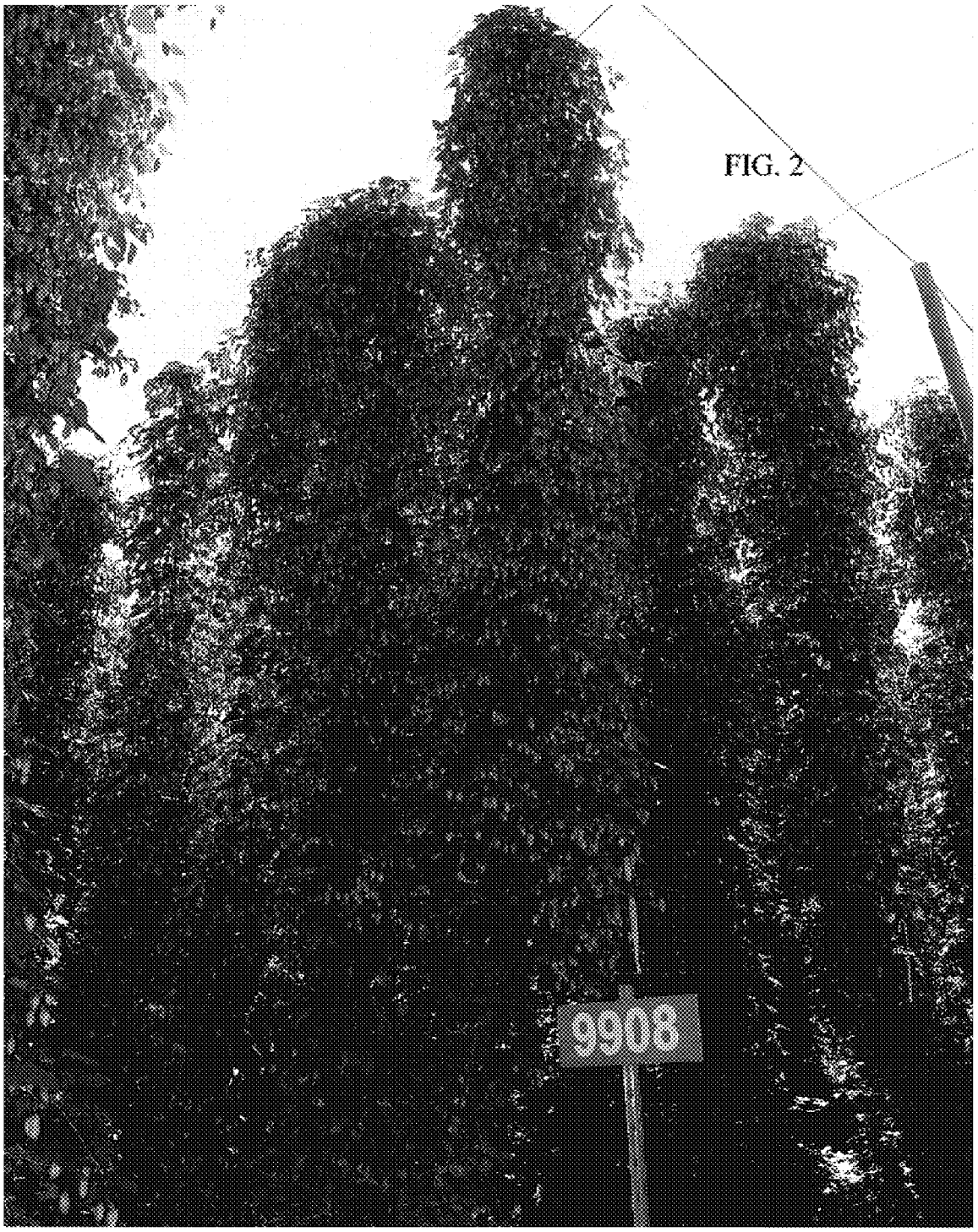
FIG. 2 depicts the appearance of the plants and cones as they are growing in the field on high trellis (18') approaching harvest time.

This description provides information on agronomic, morphological, chemical and processing characteristics of the new variety that are used in distinction and identification of a new hop variety and its parts and products by practitioners of the industries that use hops as described herein above.

General information on the botanical characteristics and cultural aspects of hops plants as they relate to agronomics, breeding and food use are particularly well discussed in the prior art, especially, U.S. Plant Pat. Nos. 10,956 and 13,132 and the literature; "Steiner's Guide to American Hops Book III", 1986; "Hops" Published by Chapman and Hall, 1991. Detailed botanical information below of the present variety is directly comparable to the prior art, as contained by reference herein.

DETAILED BOTANICAL DESCRIPTION OF THE VARIETY

The information for this botanical description was either collected or verified during the growing seasons of 2000 through 2005. Some botanical characteristics, and to a lesser degree the analytical chemical characteristics are somewhat dependent on cultural practices and climatic conditions and can vary with location and season:

1. Parentage: A hop plant originating from a controlled cross-pollination between proprietary female hop plant referred to as "98001" (not patented) with a non-patented male hop plant USDA 19058m (not patented).
2. Locality where grown and observed: North of Prosser, Wash.
3. Agronomic factors: Dates of first and last harvest are approximately September 15 and September 25. Shoots of "Super Galena" emerge from winter dormancy approximately 1 week later than the commercial variety "Zeus" and 1 week earlier than the commercial variety "Galena". Emergence is typically by April 1$^{st}$ Initial stem or shoot growth rate is average when compared to "Zeus", but faster when compared to "Galena" and slower when compared to "Nugget". After spring pruning, growth continues to be average when compared to other commercial varieties. The main vine stems are green (RHS 146D) and slightly hexagonal in cross-section shape. Inflorescence of "Super Galena" begins to appear in early July and mature during the third week of September. Cone shape is fairly uniform in the "Super Galena" variety. The hop cones of "Super Galena" are well adapted to mechanical harvest because of their compactness and ovoid shape. The cones do not shatter during harvest. In the following description color code designations are by reference to the R.H.S. Colour Chart, 4$^{th}$ Edition, provided by The Royal Horticultural Society of Great Britain.
4. Plant characteristics: Plant: vigorous, climbing vine. Plant shape: clavate. Bine color green (RHS 146D). Bine stripe: absent. Bine inter-node length (at 6' high): 24 cm. Bine diameter (at 6' high): 1 cm. Bine length: 20–24'. Stipule direction: outward up. Stipule color: green (RHS 146C). Petiole length: 8 cm. Petiole color green (RHS 144A). Petiole shape: slightly channeled (flat upper surface). Leaf arrangement: opposite. Leaf shape: cordate — palmate. Leaf color — upper surface — dark green — (RHS 137A). Leaf color — lower surface — light green — (RHS 147B). Mature leaf width: 13–15 cm. Mature leaf length: 15 cm. Number of leaf lobes: three–five. Venation pattern: Reticulate. Vein color — yellow green (RHS 145B). Leaf margin: lightly serrate to dentate. Lateral length (at 6' high): 1–1.2 m. Internode length of Lateral (at 6' high): 10–15 cm.
5. Reproductive organs; cones, seeds, parts of cones: Bract color — (RHS 144A). Bract tips shape: acute to cuspidate. Bract tip position: mostly appressed, some bracts are slightly everted at full maturity. Bract diameter: 1.2 cm. Bracteole shape: lanceolate. Bracteole color — (RHS 145C). Compactness: tight to semi-dense. Shape: ovoid to cylindrical. Cone length: 4 cm. Cone tip shape: pointed. Cone weight: 190–230 mg. Strig: compact, with modal diameter. Lupulin glands — The cone of the present variety contains numerous lupulin glands. Yield per acre: 2500–2800 pounds on average. However, this yield is contingent upon temperature, soil conditions and cultural practices, and is therefore not distinctive of the present variety. Date of maturity: — considered to be late (Sept. 15–30) as compared to other common hop varieties grown in central Washington. Seeds: highly variable in color and size depending on male parent.
6. Analytical data of cones: % Alpha-Acids (bale): 13.0–16.0% (ASBC Spectrophotometric method). % Beta-Acids (bale): 8.0–10.0% (ASBC Spectrophotometric method). Alpha/beta ratio: 1.5–1.7. Cohumulone (% of alpha-acids): 34–40%. Storage characteristics: 20–22% transformation of alpha acids after 6 months at 22° C. Total oils (mls/100 g): 1.5–2.5. Humulene (% of total oils): 19–24%. Caryophyllene (% of total oils): 6–14%. Humulene/Caryophyllene ratio: 2.3. Farnesene (% of total oils): <1.0%. Myrcene (% of total oils): 45–60%.
7. Disease resistance: The variety "Super Galena" is tolerant to hop downy mildew fungus and resistant to the strains of powdery mildew fungus found in the Yakima valley as of 2005, but since not all strains are present no future powdery mildew resistance can be assured. "Super Galena" is tolerant to strains of Verticillium wilt and the virus diseases found in the USA grown areas. Tolerance to the major soil borne pests that affect hops is not known at this time but "Super Galena" appears to be susceptible to Phytophthora root rot.
8. Regional adaptation: The "Super Galena" variety is well adapted to the drier growing regions of Washington State, specifically the Yakima Valley. "Super Galena" has not been tested in other growing locations.
9. Ploidy: Hop variety "Super Galena" is diploid. The mother is diploid and the father is diploid.

10. Life expectancy: Indefinite similar to other hop varieties.
11. Use: Flavoring and conditioning of beverages and foods and use as vegetable. Constituent of herbal remedies, nutraceuticals, pharmaceuticals, drugs, ointments, antiseptic washes and cosmetics for humans and animals. Constituent of fodder, bedding, compost, agricultural treatments, phytoremediation treatments, water and soil treatments, conditioning of fermentation and other industrial processes. Used in breeding novel hop varieties.
12. Propagation status: "Super Galena" rootstock and plant propagation material exists. Asexual plant propagation has been demonstrated.
13. Reproductive status: "Super Galena" is fertile and produces seeds upon pollination with male hop plants.

DISTINGUISHING CHARACTERISTICS

This new hop variety "Super Galena" can be distinguished from all other USA commercial varieties by its resistance to powdery mildew in combination with a high percentage of alpha and beta acids and excellent yield.

The invention claimed is:

1. A new and distinct hop plant named "Super Galena" as herein described and illustrated with a high percentage of beta acid, exceptional yield, and resistance to hop powdery mildew strains found in Washington.

* * * * *

UNITED STATES PATENT AND TRADEMARK OFFICE

CERTIFICATE OF CORRECTION

PATENT NO. : PP20,227 P3
APPLICATION NO. : 11/344257
DATED : August 18, 2009
INVENTOR(S) : Jeske et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 324 days.

Signed and Sealed this

Seventh Day of September, 2010

David J. Kappos

David J. Kappos
*Director of the United States Patent and Trademark Office*